United States Patent [19]

Kheiri

[11] Patent Number: 5,207,984
[45] Date of Patent: May 4, 1993

[54] BLOOD SAMPLE COLLECTION AND TEST DEVICE

[75] Inventor: Mohammad A. Kheiri, Elkhart, Ind.

[73] Assignee: Miles Inc., Elkhart, Ind.

[21] Appl. No.: 667,047

[22] Filed: Mar. 11, 1991

[51] Int. Cl.[5] .......................................... G01N 21/00
[52] U.S. Cl. ...................................... 422/58; 422/55; 422/56; 436/165; 436/169; 435/970; 128/760; 356/244
[58] Field of Search ..................... 422/55, 56, 57, 58; 436/164, 165, 169; 435/805, 970; 356/244; 128/760, 767; 118/31.5

[56] References Cited

U.S. PATENT DOCUMENTS

| | | | |
|---|---|---|---|
| 3,876,377 | 4/1975 | Cinqualbre | 422/58 |
| 4,387,972 | 6/1983 | Valencia | 356/244 X |
| 4,576,185 | 3/1986 | Proud et al. | 128/760 |
| 5,006,309 | 4/1991 | Khalil et al. | 422/58 X |

FOREIGN PATENT DOCUMENTS 0376135 7/1990 European Pat. Off. ............. 422/58

Primary Examiner—James C. Housel
Assistant Examiner—Maureen M. Wallenhorst
Attorney, Agent, or Firm—Roger N. Cor

[57] ABSTRACT

A test device having a semicrater sample application site attached or associated with a substrate. The semicrater sample application site has walls of nonuniform height surrounding the area designed to receive the application of sample. In particular, the walls of the semicrater on one side are higher than the walls of the semicrater on the opposite side. This facilitates the application of a small amount of sample directly onto the desired sample application site.

4 Claims, 2 Drawing Sheets

BLOOD SAMPLE COLLECTION AND TEST DEVICE

FIELD OF THE INVENTION

This invention relates to a test device or test strip sample delivery means. More particularly, the present invention relates to a "semicrater" sample application site for a test device. The "semicrater" comprises a recessed semicircular well open on one or more sides for the application of a fluid sample.

BACKGROUND OF THE INVENTION

Reagent test devices or reagent strips designed to measure analytes, such as glucose, protein, ketone and the like, present in body fluids are well known. Typically, such reagent test devices are constructed to have a reagent pad attached to one end of an elongated substrate which also serves as a handle for the test device. After the reagent pad of the test device has come into contact with a body fluid, such as urine or blood, the colorimetric reaction which occurs in the reagent pad is measured either visually or instrumentally. For visual determinations the reagent pad is normally compared to a standardized color chart. If an instrument is used a beam of light from the instrument is directed onto the reagent pad and the light reflected from the pad is measured.

Typically, a blood sample is applied to the reagent pad of a reagent test device by pricking a finger with a lance or needle and then applying a drop of blood directly to the surface of the reagent pad. Since the reagent pad is normally in an elevated position relative to the substrate of the reagent test device, application of the blood sample can be made with relative ease. However, it is difficult for some individuals to obtain even a small drop of blood to be used as a sample. For this and other reasons there has been a trend toward making the sample application site or reagent area very small. While this means that less sample is required it also means that the application of sample to the sample application site is more difficult.

Diabetics, in particular, tend to have difficulty applying a small blood sample to a small reagent area. One reason for this is the fact that the necessity of repeatedly pricking a finger to obtain a suitable specimen tends to leave diabetics with a loss of feeling or sensitivity in the ends of their fingers and this means that they must rely almost entirely on sight to correctly apply a blood sample to the desired area of a reagent pad. However, another problem faced by diabetics, and particularly with older diabetics, is with the loss of vision or eyesight. Thus, the person required to use the test device may not have good vision.

A further problem which can occur with the use of diagnostic test devices is the fact that the sample applied to a test device does not make good contact with the sample application site. The reason for this is the fact that the person using the test device simple does not place the blood sample at the right location or does not apply sufficient blood sample to adequately cover the area of the reagent pad. Diabetics often have shaky hands either due to age, complications of the disease, or because of low or high sugar levels at the time of providing a blood sample. For such individuals support and guidance of a finger while applying a sample of blood onto a reagent area are highly desirable.

Accordingly, there is a need for means to simplify the positioning of sample onto a reagent test device or test strip without the necessity of making the reagent pad large and without requiring a very large sample. The present invention achieves these goals, eliminating the necessity for large reagent application sites and large sample sizes. In addition, the present invention facilitates the application of sample directly onto the reagent pad in a manner that sample placement and sample volume are eliminated as problems.

SUMMARY OF THE INVENTION

An object of the present invention is to provide simple and effective means for applying a body fluid to a selected area of a reagent test device.

Yet another object of the present invention is to provide means for permitting a small sample to be quickly and correctly applied to a sample application site of a reagent test device.

Another object of the present invention is to provide an inexpensive and effective means for aiding the positioning of a specimen of sample directly onto a sample application site without visual aid.

A still further object of the present invention is to provide a test means or test strip which eliminates sample volume and sample placement problems associated with conventional test means having a flat reagent pad located at one end of an elongated substrate for the application of sample.

In accordance with the present invention a reagent test device is formed with a semicrater surrounding and positioned above the sample application site. The semicrater is formed as a small well with one portion or side lower than another one. By introducing a specimen sample from the lower side of the semicrater the sample is quickly and correctly applied directly to the desired location on the reagent test device in contact with the reagent application site without trapping air bubbles. The raised side of the semicrater helps to initially guide the application of the sample specimen and contain all of the sample in the correct position. This means that a very small sample size can be used since all of the sample is channeled or applied to the correct location where good contact6 is made with the reagent pad or transfer layer of the reagent test device.

The cup shaped semicrater also provides a scraping edge so that the user can direct all of a blood drop from his/her finger into the cup. The shape of the cup provides one with poor vision with something to feel and thus provides and application target for the sample. The rim of the semicrater or cup permits one to rest his/her finger which is important to reduce any shaking while applying the sample. The cup like configuration also acts like a reservoir which assures that sufficient blood is applied to the reagent test device.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
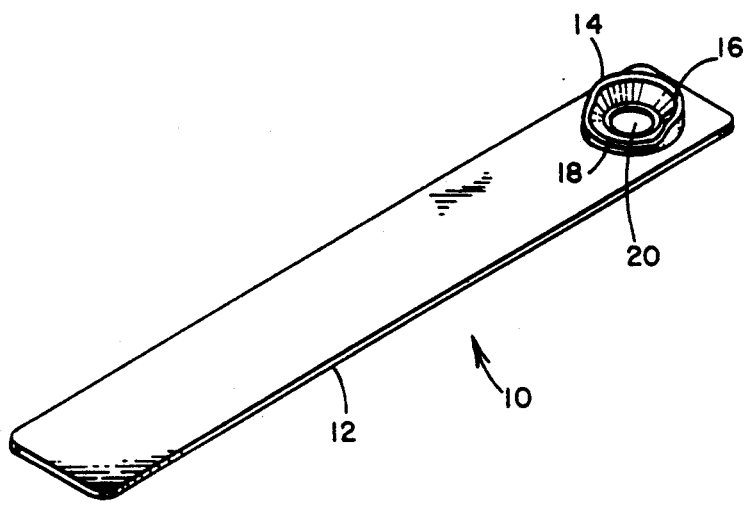
FIG. 1 is a diagrammatic perspective view illustrating a reagent test device in accordance with the present invention in which a semicrater is formed as part of the substrate to surround the sample application site.
Figure 2:
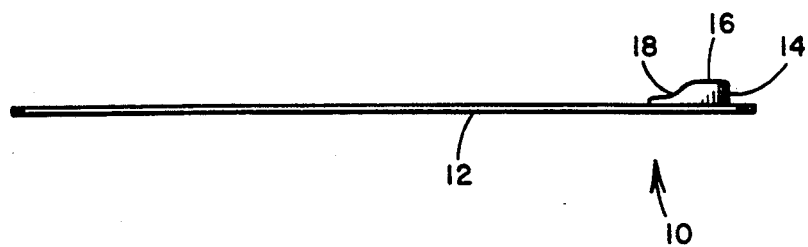
FIG. 2 is a side view of the reagent test device of FIG. 1.

Referring to the drawings, FIGS. 1 and 2 illustrate a reagent test device 10 having an elongated substrate 12 with a semicrater 14 located at one end. The semicrater 14 has a raised portion 16 constituting one side of the semicrater and a lower portion 18 on an opposite side of the semicrater. In practice the semicrater can conveniently be molded or formed at the same time as the substrate using the same material, typically a plastic. The semicrater 14 surrounds a sample application site 20.

Since the semicrater 14 effectively concentrates the sample inside the well of the semicrater directly at the desired sample application site 20 the resulting test device 10 requires only a very small sample.

In use the sample, e.g., a drop of blood, is applied to the sample application site 20 of the reagent test device 10 by bringing the sample to the open side of the semicrater 14. The correct placement of the sample is easily determined from contact with the raised portion 16 of the semicrater 14. In addition, the raised portion 16 of the semicrater 14 helps to retain all of the sample inside the well-like semicrater 14 in direct contact with the sample application site 20.

By using a semicrater 14 rather than a full "crater" or "well" it is possible to make certain that the sample contacts the sample application site 20, consisting of a reagent pad or a transfer layer such as a spreading layer or filter layer, each time sample is applied. The semicrater eliminates any air bubble trapped between the blood and the reagent since it permits the air bubble to escape from the open side of the semicrater. If a full crater or well used the size of the crater would have to be sufficiently large to actually be able to apply the sample directly inside the crater onto the sample application site to assure that contact is made between the sample and the sample application site. If a full crater constituted only a small well there would be the possibility, and indeed the high probability, that trapped air or adhesion of the sample to side walls of the well would prevent the sample from actually contacting the sample application site. Without good contact between the sample and the sample application site the test results would be adversely affected and individual tests would have to be repeated until good contact occurs.

If desired, the semicrater can be partially covered by a shield or partial dome (not shown) to protect the sample application site 20 and hence the reagent area from ambient light. Ambient light can adversely affect the storage life of the reagent(s) which is/are used and can also affect the measurement made of colorimetric change caused by reaction of sample with the reagent. Thus, a cover over a portion of the semicrater could help to shield the sample application area and overcome these problems.

It is sometimes desirable to also incorporate an air vent into the substrate to make certain that blood flows smoothly and uniformly onto the reagent surface or any layer covering the reagent surface. Also an air vent assures that oxygen is supplied to the reagent present in the sample application site and/or that air bubbles do not form in the sample application site which would interfere with the contact made between the sample and the reagent matrix.

Figure 3:
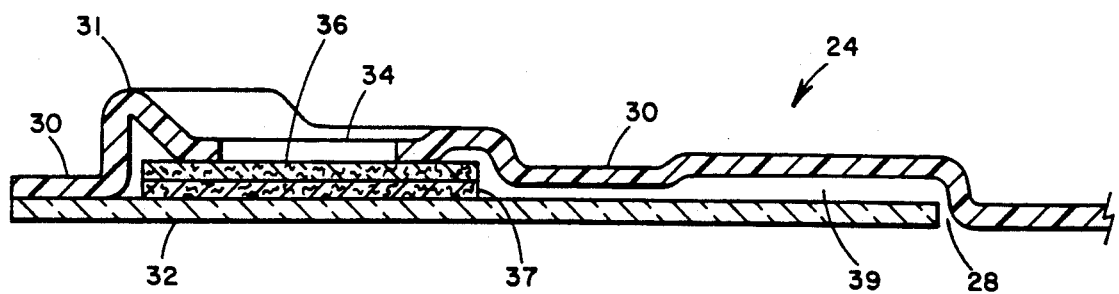
FIG. 3 is a partial side view, in cross section, of another embodiment of a test device in accordance with the present invention.

FIG. 3 illustrates a test device 24 in accordance with the present invention which has an air vent 39 connected to a vent opening 28. The air vent 39 is formed between an upper layer 30 and a lower layer 32 of test device 24. One end of layer 30 is configured to form a semicrater like sample application site 34 surrounded by center 31. Lower layer 32 is made from a suitable material, such as a clear plastic, which permits the color development in the test device 24 to be determined from the bottom of the test device. Polycarbonate, polystyrene, polypropylene and other homo and copolymers can be used as a suitable lower layer 32. To provide firmness to the test device 24 it is desirable to have the lower layer 32 laminated to the upper layer 30 for the entire length of the test device. Sandwiched between layers 30 and 32 at sample application site 34 are a filter 36 and a reagent layer 37. The filter 36 can be formed from any suitable material, such as glass fibers, to aid in filtering the sample applied to test device 24 and aid in distributing the sample evenly over reagent layer 37. Thus, filter 36 can be used to remove red blood cells and other materials which might interfere with color development occurring in the reagent layer 37. Excess sample can escape along air vent 39. Thus, by incorporating an air vent 39 into test device 24 excess sample is removed from the area of measurement and can be maintained entirely within the test device. This is important not only in assuring the correct use of the test device but also in assuring the safe handling of the sample being measured.

Figure 4:
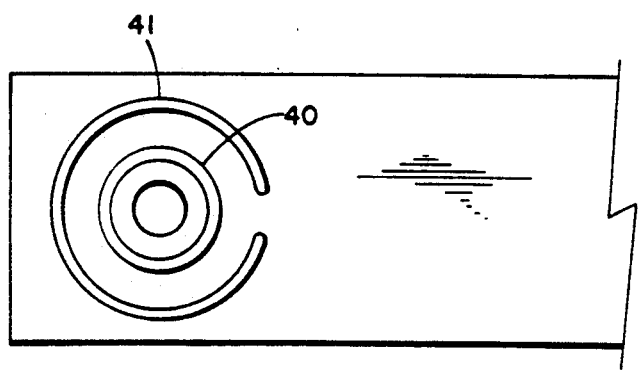
FIGS. 4 and 5 are partial top views of yet other embodiments of test devices in accordances with the present invention.
Figure 5:
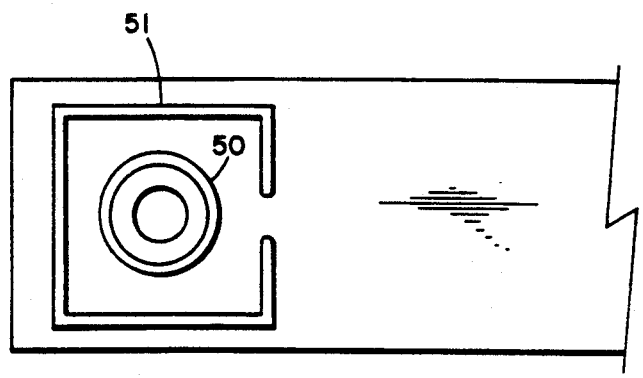

FIGS. 4 and 5 illustrate other modifications of the invention in which the semicrater areas 40 and 50, respectively, are surrounded by raised ribs 41 and 51, respectively. The raised ribs 41 and 51 are present to contain excess sample. These ribs can be present even if the test device has a reservoir to contain excess sample. The reason for this is the fact that some samples absorb very slowly into the reagent material and need to be contained prior to being absorbed. When test devices are constructed with raised ribs around the semicrater it is desirable that the minimum width of the test device be 0.50 inch (1.27 cm) so excess sample can be maintained on the test device while the test device is inserted into an instrument.

From the foregoing, it will be seen that this invention is well adapted to attain all of the ends and objects heretofore set forth, together with other advantages which are obvious and inherent. The unique design of the semicrater-like sample application site for a test device provides a simple and effective means for applying a body fluid to a selected area of the test device. In one embodiment of the invention the substrate used as the support or handle of the test device and the semicrater sample application site can be formed as one molded piece from a suitable plastic material, such as polystyrene. Using the semicrater sample application site permits the sample size to be reduced. It permits a small sample to be quickly and correctly applied to the sample application site. The semicrater provides an inexpensive and effective means for aiding the positioning of a specimen directly onto the sample application site without other external assistance. This is particularly important for older individuals and for individuals having poor eyesight. Another advantage of the invention is the fact that the sample is confined to the area inside the semicrater and there is less possibility of contamination. Accordingly, the test devices of the present invention provide an improved safety factor which is important in view of the hazards associated with aids, hepatitis, etc.

Obviously, many modifications and variations of the invention as heretofore set forth can be made without departing from the spirit and scope thereof and therefore only such limitations should be imposed as are indicated by the appended claims.

What is claimed is:

1. A test device consisting essentially of:
   (a) an elongated strip,
   (b) a sample delivery means, disposed on a surface of said strip, wherein said sample delivery means has an open, circular bowl shaped configuration with an open bottom and with walls extending vertically from said surface of said strip and wherein the walls forming a portion of said bowl shaped configuration of said sample delivery means are lower than the walls of an opposite portion of said bowl shaped configuration of said sample delivery means, and
   (c) a reagent pad secured to the strip and positioned beneath the open bottom of the circular bowl shaped configuration of the sample delivery means.

2. The test device of claim 1 wherein the strip and sample delivery means constitute one molded piece.

3. The test device of claim 1 wherein the walls of said sample delivery means partially shield the reagent pad from ambient light.

4. The test device of claim 1 wherein the elongated strip is rectangular in shape and wherein the sample delivery means is located at one end of said strip.

* * * * *